US007985430B2

(12) United States Patent
Levine et al.

(10) Patent No.: US 7,985,430 B2
(45) Date of Patent: *Jul. 26, 2011

(54) SOLID MUCOADHESIVE COMPOSITION

(75) Inventors: William Levine, Jerusalem (IL); Aron Satter, Belt Shamesh (IL)

(73) Assignee: Izun Pharmaceuticals Corporation, Dover, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/536,800

(22) PCT Filed: Mar. 3, 2003

(86) PCT No.: PCT/IL03/00159
§ 371 (c)(1), (2), (4) Date: Jan. 17, 2006

(87) PCT Pub. No.: WO2004/047813
PCT Pub. Date: Oct. 6, 2004

(65) Prior Publication Data
US 2006/0228427 A1 Oct. 12, 2006

(30) Foreign Application Priority Data
Nov. 27, 2002 (IL) ......................................... 153124

(51) Int. Cl.
*A61K 36/00* (2006.01)
*A61K 36/28* (2006.01)
(52) U.S. Cl. ........ 424/725; 424/737; 424/774; 424/777; 424/778; 424/779
(58) Field of Classification Search .................... None
See application file for complete search history.

(56) References Cited

U.S. PATENT DOCUMENTS

| | | | |
|---|---|---|---|
| 4,740,365 A | | 4/1988 | Yukimatsu et al. |
| 4,742,046 A | * | 5/1988 | Bliah .............................. 514/8 |
| 5,162,037 A | | 11/1992 | Whitson-Fischman |
| 5,543,154 A | * | 8/1996 | Rork et al. .................... 424/473 |
| 5,639,473 A | * | 6/1997 | Grinstaff et al. .............. 424/450 |
| 5,723,143 A | | 3/1998 | Jacques et al. |
| 5,780,046 A | * | 7/1998 | Humber et al. ............... 424/440 |
| 5,863,553 A | * | 1/1999 | Britton et al. ................. 424/433 |
| 6,039,949 A | | 3/2000 | Pero |
| 6,217,908 B1 | * | 4/2001 | Mathiowitz et al. .......... 424/493 |
| 6,350,784 B1 | | 2/2002 | Squires |
| 6,428,819 B1 | | 8/2002 | Lavie et al. |
| 2002/0044964 A1 | | 4/2002 | Bologna et al. |
| 2002/0136755 A1 | * | 9/2002 | Tyrrell et al. ................. 424/443 |
| 2002/0165169 A1 | * | 11/2002 | Kim et al. ........................ 514/27 |
| 2003/0003140 A1 | * | 1/2003 | Domb et al. ................... 424/449 |
| 2003/0018009 A1 | * | 1/2003 | Collins ........................... 514/52 |
| 2004/0151789 A1 | * | 8/2004 | Levine et al. ................. 424/729 |

FOREIGN PATENT DOCUMENTS

| | | |
|---|---|---|
| WO | 98 42188 | 10/1998 |
| WO | WO 99/20289 | * 4/1999 |
| WO | 99/55312 | 11/1999 |
| WO | 02/094300 | 11/2002 |

OTHER PUBLICATIONS

1001herbs http://www.1001herbs.com/elderberrycombo/ prior art date: 2000.*
Holistic-online http://www.holistic-online.com/herbal-med/_Herbs/h18.htm prior art date: 2000.*
1001 Herbs prior art date; 1998 http://web.archive.org/web/19981207055325/http://1001herbs.com/elderberrycombo/.*
International Search Report for PCT/IL03/00159 dated Jun. 18, 2003.
"Martindale—The Extra Pharmacopeia, $30_{th}$ Ed.", 1993, The Pharmaceutical Press, London, XP002211675 (Preparations: Echinacea Rö-Plex, Sambucus Complex, Sinotar as listed on XP-002211675).
Page, "Milestones in Periodontal Research and the Remaining Critical Issues," Journal of Periodontal Research, 1999, vol. 34, pp. 331-339.
Chavez et al; "Saint John's Wort"; Hospital Pharmacy, Lippincott, Philadelphia, US, vol. 32, No. 12, 1997, pp. 1621-1628 and 1631-1632, XP000913486.
Bauer: "*Echinacea*-Drogen-Wirkungen Und Wirksubstanzedn"; Zeitschrift Fuer Aerztliche Fortbildung, Jena, DD, vol. 90, 1996, pp. 111-115, XP000198717.
Serkedjieva et al; "Antiviral Activity of the Infusion (SHS-174) From Flowers of *Sambucus nigra* L., Aerial Aprts of *Hypericum perforatum* L., and Roots of *Saponaria officinalis* L. Against Influenza and Herpes Simplex Viruses"; Phytother Res., vol. 4, No. 3, 1990, pp. 97-100, XP001099138.
Hans Braun: "Heilpflanzen-Lexikon Fur Arzte Und Apotheker", 1981, Gustav Fisher Verlag, Stuttgart, pp. 68-69, 197-198, 120-121 and 87. XP002211676.
J. Bruneton: "Pharmacognosy Phytochemistry Medicinal Plants"; 1999, Lavoisier Publishing, Paris, pp. 175, 703-704, 441-442 and 366-367, XP002211677.
"*Echinacea*"; Honest Herbal: A Sensible Guide to the Use of Herbs and Related Remedies, Pharmaceutical Products Press, New York, NY, US, 1993, pp. 115-117, XP002914645.
Brinkhaus et al; "Chemical Pharmacological and Clinical Profile of the East Asian Medical Plant *Centella asiatica*"; Phytomedicine: International Journal of Phytotherapy and Phytopharmacology. Germany, Oct. 2000, vol. 7, No. 5, pp. 427-448, XP002211674.
Ceschel et al., "Design and Evaluation of Buccal Adhesive Hydrocortisone Acetate (HCA) Tablets", Drug Delivery, vol. 8, pp. 161-171.

* cited by examiner

*Primary Examiner* — Michele Flood
*Assistant Examiner* — Catheryne Chen
(74) *Attorney, Agent, or Firm* — Nixon & Vanderhye P.C.

(57) ABSTRACT

An adhesive solid therapeutic composition containing an active ingredient which is an extract of a plant selected from the group consisting of *Sambucus nigra, Centella asiatica* and *Echinacea purpurea*, or mixtures thereof and excipients, said excipients comprising (i) a bulk ingredient (ii) an adhesive polymer of acrylic acid and (iii) polyvinylpyrrolidone.

15 Claims, No Drawings

SOLID MUCOADHESIVE COMPOSITION

This application is the US national phase of international application PCT/IL2003/000159, filed 3 Mar. 2003, which designated the U.S. and claims benefit of IL 153124, filed 27 Nov. 2002, the entire contents of each of which are hereby incorporated by reference.

FIELD OF THE INVENTION

The present invention relates to an adhesive solid dosage form containing a mixture of herbal extracts as the active ingredient, suitable particularly for the treatment of mucosal lesions.

BACKGROUND OF THE INVENTION

Oral diseases constitute a diverse group of conditions that are responsible for much human suffering. In addition to diseases of the hard tissues of the oral cavity (e.g. dental caries), there are many different pathological conditions affecting the oral mucosa and periodontal tissues. This group includes the commonly found conditions such as gingivitis, periodontal disease, aphthous ulceration and *Herpes simplex* lesions, as well as the oral manifestations of the less common vesicular-bullous conditions such as bullous pemphigoid, pemphigus, erythema multiforme and lichen planus, as well as many other inflammatory conditions of autoimmune origin.

In some circumstances, localized lesions of the oral (and other) mucosal tissues may be treated by systemic treatment regimes. However, in many cases, systemic management may either be ineffective or be accompanied by unacceptable adverse effects.

While methods of local treatment of mucosal lesions do exist, many of these methods are not particularly effective. For example, medicaments given as lozenges may be partly absorbed into the systemic circulation by way of the mucosal blood vessels, while not achieving a sufficiently high concentration at the lesion site. Other medicaments, such as those intended for relief of painful ulcerative lesions are sometimes administered in the form of ointments, lotions or pastes. These are often difficult to apply, as they do not adhere to the normally moist mucosal surface, which therefore needs to be dried before using these preparations in order to achieve greater adhesion. In addition, pastes and ointments suffer from the disadvantage that they are often difficult to apply to a small, localized area, there being a tendency to spread to adjacent healthy tissue. This problem, combined with rapid dissolution of the thin layer of cream or ointment results in a rapid loss of the desired therapeutically effective concentration at the lesion site. Finally, with most preparations for topical use on mucosal membranes, it may be impossible to maintain sustained delivery to the lesion either because of rapid dissolution of the preparation (e.g. with lozenges, pastilles etc.) or because of systemic absorption, as mentioned hereinabove.

With many oral soft-tissue conditions, regardless of whether these are due to mechanical, thermal or chemical trauma, localized infection, or autoimmune disorders, rapid, initial, relief may be obtained by physically covering the lesions.

Several solid mucoadhesive formulations, and specifically tablets, for use on the skin and/or mucosal tissues have been described in the literature. However, the production of these tablets generally meets with a difficulty associated with the poor flow properties of the mixture containing the sticky components.

It is a purpose of the present invention to provide a solid composition comprising a therapeutic herbal composition for adhesive application to the oral mucosa.

It is another object of the invention to provide a solid composition that overcomes the problems associated with the large-scale industrial production of adhesive mixtures having poor flowability characteristics, without diminishing from the adhesiveness of the composition.

It is a further purpose of the invention to provide such solid composition that overcomes the problems and disadvantages of prior art solid compositions.

Further objects and advantages of the present invention will become apparent as the description proceeds.

SUMMARY OF THE INVENTION

The present invention is primarily directed to an adhesive, solid therapeutic composition containing an active ingredient comprising an extract of a plant selected from the group consisting of *Sambucus nigra, Centella asiatica* and *Echinacea purpurea*, or mixtures thereof, and excipients, said excipients comprising (i) a bulk ingredient, which is preferably lactose, (ii) an adhesive polymer of acrylic acid and (iii) polyvinylpyrrolidone.

The inventors have unexpectedly found that the combination of the herbal active ingredient(s) with the excipients defined above may be effectively formulated as a flat tablet suitable for local administration to the oral mucosa, which tablet exhibits excellent adhesiveness and hardness. According to a particularly preferred embodiment of the invention, the tablet has unique structural characteristics, the surface of the tablet being partially coated with non-adhesive coating, such that one face of the tablet is rendered non-adhesive. The tablet is administered to the patient by contacting the adhesive face of the tablet with the mucosal site to be treated, whereas the coated, non-adhesive face projects away from said site to be treated, thereby preventing undesired adhesion of said tablet with other mucosal tissues, and in particular, the lingual mucosa. Thus, one aspect of the invention relates to a mucoadhesive tablet comprising an active ingredient which is an extract of a plant selected from the group consisting of *Sambucus nigra, Centella asiatica* and *Echinacea purpurea*, or mixtures thereof, and excipients, said excipients comprising (i) a bulk ingredient, which is preferably lactose, (ii) an adhesive polymer of acrylic acid and (iii) polyvinylpyrrolidone, wherein the surface of said tablet is partially coated with a non-adhesive material, such that said tablet is provided with a first, adhesive side and a second, coated, non-adhesive side.

In one particularly preferred embodiment of the invention, the active ingredient is a mixture of extracts of the plants *Sambucus nigra, Centella asiatica* and *Echinacea purpurea*.

According to a preferred embodiment of the invention, the weight ratio between the polyacrylic adhesive polymer component and the polyvinylpirrolidone component is in the range of 5:7 to 7:5, with the weight percent of said components (in relation to the total weight of the tablet of the invention) being preferably in the range of 20 to 40% and more preferably in the range of 25 to 35%.

Preferably, the adhesive, solid therapeutic composition according to the invention comprises 0.1 to 15 by weight percent of the active herbal ingredient(s), 50 to 65 by weight percent lactose, 10 to 20 weight percent of an adhesive polymer of acrylic acid which is preferably CARBOPOL 974P (available from the Lubrizol Corporation), and 10 to 20 weight percent of polyvinylpyrrrolidone, which is preferably povidone K-90 or povidone K-29-32.

The adhesive, solid therapeutic composition according to the invention may further comprise a lubricant, which is preferably magnesium stearate, a flow agent, which is preferably colloidal silicon dioxide, and one or more flavoring agents.

According to another embodiment of the invention, the composition comprises an adhesive polymer of cellulose derivative, which is preferably hydroxypropyl cellulose KLUCEL XHF (available from Hercules Inc.).

All the above and other characteristics and advantages of the present invention will be further understood from the following illustrative and non-limitative description of preferred embodiments thereof.

DETAILED DESCRIPTION OF PREFERRED EMBODIMENTS

The adhesive solid composition of the present invention, as disclosed herein, comprises extracts of one or more plants. It is to be noted that the term "extract" is used herein to include all of the many types of preparations containing some or all of the active ingredients found in the relevant plants. Thus the extracts may be produced by cold extraction techniques using a variety of different extraction solvents including, but not limited to, water, fatty solvents (such as olive oil), and alcoholic solvents (e.g. 70% ethanol). Cold extraction techniques are usefully applied to softer parts of the plant such as leaves and flowers, or in cases wherein the desired active components of the plant are heat labile. Alternatively, the aforementioned solvents may be used to produce extracts of the desired plants by a hot extraction technique, wherein said solvents are heated to a high temperature, the precise value of said temperature being dependent on the properties of the chosen solvent, and maintained at that temperature throughout the extraction process. Hot extraction techniques are more commonly applied to the harder, tougher parts of the plant, such as bark, woody branches and larger roots. In some cases, sequential extractions need to be performed in more than one solvent, and at different temperatures. Finally, pharmacologically-active extracts may also be produced by means of critical-point extraction with, for example, liquid carbon dioxide.

Standard procedures for producing plant extracts (including hot extraction, cold extraction and other techniques) are described in many publications including "Medicinal plants: a field guide to the medicinal plants of the Land of Israel (in Hebrew), author: N. Krispil, Har Gilo, Israel, 1986"and "Making plant medicine, author: R. Cech, pub. by Horizon Herbs, 2000".

Mixtures of extracts of different plant species (such as those of the present invention) may be prepared using different ratios of each extract. For example, in a particularly preferred embodiment, the composition of the present invention preferably comprises a mixture of extracts of *Centella asiatica, Echinacea purpurea* and *Sambucus nigra* in the following range of weight ratios: 0.5-7:0.5-3:2-25

For example, in one embodiment of the tablet of the invention, the weight of which is 100 mg, the following mixture of herbal extracts is present: 3.42 mg of *Sambucus nigra*, 0.8 mg of *Centella asiatica* and 0.07 mg *Echinacea purpurea*.

In order to treat a mucosal lesions in patient with an adhesive, solid therapeutic composition of the present invention containing a mixture of herbal extracts as described hereinabove, it is necessary to administer said composition in a therapeutically-effective amount, that is, in an amount that will provide a concentration of the herbal extracts at the treatment site that is capable of exerting the desired therapeutic effect. It has been found, in general terms, that the solid composition of the present invention need to be administered in amounts such that, typically, each tablet contains between 0.05 mg and 15 mg (dry weight) of each herbal extract.

It is necessary to administer the solid composition of the present invention for periods of time that are sufficient to allow optimal contact of the therapeutically effective amounts of the herbal extracts with the lesions to be treated. Typically, the composition disclosed herein needs to remain in contact with the lesion to be treated for a period of between 1 and 5 hours. This treatment may be repeated up to 5 times each day, as required, and as determined by a competent clinician.

According to one preferred embodiment of the invention, the adhesive, solid therapeutic composition is provided in the form of an adhesive tablet suitable for buccal administration. The composition of the invention, however, may also be administered (either in the form of an adhesive tablet or any other suitable form) to other mucosal tissues, including, but not limited to, the anal and vaginal mucosae. The tablets may be obtained using methods well known in the art, which typically involve mixing of the various ingredients and wet granulating said mixture, following which the granules are dried, milled and compressed to yield the tablets.

Preferably, the procedure for producing the tablets according to the present invention comprises mixing the bulk ingredient, which is most preferably lactose, with a partial amount of the polyvinylpyrrolidone, which is preferably povidone K-90, and wet granulating said mixture in water, following which the resultant granules are dried and milled. The mixing operation is preferably carried out using a high-shear mixer. The subsequent drying and milling are typically carried out using a fluid bed drier, at 100° C., and conventional milling equipment.

The dry, milled granulate obtained is mixed with active extracts of one or more of the plants *Sambucus nigra, Centella asiatica* and *Echinacea purpurea*, the adhesive polymer of polyacrylic acid, which is preferably CARBOPOL 974P and the additional amount of povidone K-90, and, optionally, with an adhesive polymer of a cellulose derivative, which is preferably hydroxypropyl cellulose (KLUCEL XHF) and, if desired, with flow agents, such as colloidal silicon dioxide and flavoring agents. The mixing operation is preferably carried out in a V-shaped blender for several minutes. A lubricant, which is most preferably magnesium stearate, is introduced at this stage into the resultant mixture, and the blending is continued for additional one to three minutes. The mixture may be compressed using a rotary tableting machine to produce the core tablets.

According to a particularly preferred embodiment of the invention, the tablet obtained following the compression stage is partially coated, such that a non-adhesive coating is produced on one side (or face) of the tablet, whereas the other side of the tablet retains the adhesive properties attributed to the surprising combination of the active ingredient with the polyacrylic component and polyvinylpirrolidone. To this end, a perforated plate is positioned on a suitable surface, the thickness of said plate and the cross-section of the holes of said plate being essentially the same as the thickness and cross-section of the tablet, respectively, such that the tablets may be placed in said holes, their lower faces being supported on said surface. Preferably, the surface is provided with holes of small diameter, to allow run-off of residual amounts of the coating material, thus preventing undesirable accumulation of said coating material on said surface or within the holes of said plate. The upper faces of the tablets are then coated with a suitable non-adhesive, water-impermeable material, such as ethylcellulose, preferably by spraying on said upper faces an aqueous dispersion containing said non-adhesive, water-impermeable material together with one or more plasticizers, such as triethyl citrate, optionally in the presence of a color pigment, following which the tablets are dried, to yield the final, desired solid dosage form according to the present invention.

The following examples are provided for illustrative purposes and in order to more particularly explain and describe the present invention. The present invention, however, is not limited to the particular embodiment disclosed in the examples.

EXAMPLES

Example 1

955.0 g of Lactose monohydrate USP/NF, EP, BP, JP (Pharmatose DCL, 119 spary dried) and 45.0 g of Povidone USP K-90 were mixed for three minutes in high sheer mixer (KG-5, manufactured by Key Instruments), the impeller speed and the chopper speed being adjusted to 200 rpm and 2500 rpm, respectively. Water (125 g) was added to the mixture, under mixing (the impeller speed and the chopper speed being adjusted to 300 rpm and 5500 rpm, respectively) and the mixing was allowed to continue for an additional four minutes. The granulate obtained was dried in a fluid bed drier (Uniglat, manufactured by Glatt) at 100° C. The dried granulate was milled with a Quadro comill (SR:197-0678). The dried, milled granulate (282.5 g), Carbopol 974P (75 g), Silicon Dioxide colloidal (15 g), Povidone USP K-90 (75 g), the active ingredient (45 g) and Flavor Strawberry Durarom 501334 (2.5) were mixed in PK-Blender for 5 minutes, following which magnesium stearate (5.0 g, #30 sieved) was added and the mixing was allowed to continue for an additional two minutes. The composition obtained was compressed (Betapress, manufactured by Mansety), to produce 100 mg tablets of the following composition:

TABLE I

| Ingredient | Weight percent |
|---|---|
| Herbal extracts of *Sambucus nigra*, *Centella asiatica* and *Echinacea purpurea* | 9.00 |
| Lactose monohydrate | 53.96 |
| Carbopol 974 | 15.00 |
| Povidone USP K-90 | 17.54 |
| Silicon Dioxide Colloidal (Aerosil 200) | 3.00 |
| Flavour strawberry durarome 501334 | 0.50 |
| Magnesium stearate, NF | 1.00 |

The coating composition was prepared as follows: 300.0 g of an aqueous dispersion of ethylcellulose (Aquacoat ECD) and 21.6 g of triethyl citrate were mixed for 30 minutes. 1.0 g of a coloring material (FD&C Blue#1 Alum Lake) was mixed with deionized water in Silverson Homogenizer to obtain a homogeneous suspension, which was then added to the mixture comprising ethylcellulose and triethyl citrate. The composition obtained was used to coat one face of about 200 tablets, using the spraying system of perforated coating pan (Thai-F.C. 15", manufactured by Thai). The partially coated tablets were dried by means of a hot fan.

The following parameters were measured for the tablets before and after the partial coating:

TABLE II

| Property | Non-coated tablet | Partially Coated tablet |
|---|---|---|
| Average weight (mg) | 102.1 | 104.8 |
| Average hardness* (Kp) | 3.8 | 4.2 |
| Average Thickness (mm) | 1.2 | 1.2 |
| Adhesive strength** (g) | 590 | |

*The hardness was measured using Vankel VK 200 hardness Tester.
**The adhesiveness was measured according to the procedure described in Chary et al., "In Vitro and In Vivo Adhesion Testing of Mucoadhesive Drug delivery Systems", Drug Development and Industrial Pharmacy 25, pp. 685-690 (1999).

Example 2 (Comparative)

For the purpose of comparison, a tablet containing no active ingredient was prepared using the procedure described in above:

TABLE III

| Ingredient | Weight percent |
|---|---|
| Herbal extracts of *Sambucus nigra*, *Centella asiatica* and *Echinacea purpurea* | 0.00 |
| Lactose monohydrate | 62.55 |
| Carbopol 974 | 15.00 |
| Povidone USP K-90 | 17.95 |
| Silicon Dioxide Colloidal (Aerosil 200) | 3.00 |
| Flavour strawberry durarome 501334 | 0.50 |
| Magnesium stearate, NF | 1.00 |

The physical parameters of interest were determined with respect to both coated and non-coated forms of the above-described "placebo" tablet, with the following results obtained:

TABLE IV

| Property | Non-coated tablet | Partially Coated tablet |
|---|---|---|
| Average weight (mg) | 99.8 | 101.4 |
| Average hardness (Kp) | 3.6 | 4.1 |
| Average Thickness (mm) | 1.1 | 1.2 |
| Adhesive strength (g) | 372 | |

It is apparent from a comparison of the results presented in Tables II and IV that the active ingredient according to the present invention makes a significant contribution to the adhesive strength of the solid composition disclosed and claimed herein (adhesive strength with active ingredient: 590 g/without active ingredient: 372 g). This unexpected property permits the preparation of solid compositions having reduced concentrations of the adhesive polymer and/or polyvinylpyrrolidone (thereby exhibiting improved flowability characteristics), whilst not reducing the adhesive strength thereof.

Example 3

Using the general procedure described above, the following tablet was prepared:

TABLE V

| Ingredient | Weight percent |
|---|---|
| Herbal extracts of *Sambucus nigra*, *Centella asiatica* and *Echinacea purpurea* | 9.00 |
| Lactose monohydrate | 51.1 |

TABLE V-continued

| Ingredient | Weight percent |
|---|---|
| Carbopol 974 | 15.00 |
| Hydroxypropyl Cellulose (Klucel HXF) | 15.00 |
| Povidone USP K-90 | 5.4 |
| Silicon Dioxide Colloidal (Aerosil 200) | 3.00 |
| Flavour strawberry durarome 501334 | 0.50 |
| Magnesium stearate, NF | 1.00 |

The adhesive strength of the tablet was 589 g. The corresponding "placebo" tablet exhibited adhesive strength of 335 g.

The invention claimed is:

1. A muco-adhesive solid therapeutic composition containing an active ingredient that is a mixture of extracts obtained from the plant species *Sambucus nigra, Centella asiatica* and *Echinacea purpurea*, and excipients, said excipients comprising a bulk ingredient, an adhesive polymer of acrylic acid and polyvinylpyrrolidone, wherein the muco-adhesive solid therapeutic composition adheres to mucosal tissue.

2. A muco-adhesive solid therapeutic composition according to claim 1 provided in the form of a tablet, wherein the surface of said tablet is partially coated with a non-adhesive material, such that said tablet is provided with a first, adhesive side and a second, coated, non-adhesive side.

3. A muco-adhesive solid therapeutic composition according to claim 1, comprising the active ingredient in an amount from 5 to 15 percent, lactose in an amount from 50 to 65 percent, an adhesive polymer of acrylic acid in an amount from 10 to 20 percent, and polyvinylpyrrolidone in an amount from 10 to 20 percent, based on the total weight of the composition.

4. A muco-adhesive solid therapeutic composition according to claim 1 further comprising hydroxypropyl cellulose.

5. A muco-adhesive solid therapeutic composition according to claim 2 further comprising hydroxypropyl cellulose.

6. A muco-adhesive solid therapeutic composition according to claim 3 further comprising hydroxypropyl cellulose.

7. A muco-adhesive solid composition according to claim 1, wherein the muco-adhesive solid composition is structurally suitable for buccal administration.

8. A muco-adhesive solid composition according to claim 1, wherein the muco-adhesive solid composition is structurally suitable for vaginal administration.

9. A muco-adhesive solid composition according to claim 1, wherein the muco-adhesive solid composition is structurally suitable for anal administration.

10. A method of treating a mucosal tissue lesion in a patient comprising the step of contacting a mucosal tissue lesion with a therapeutically effective amount of a muco-adhesive solid therapeutic composition containing an active ingredient that is a mixture of extracts obtained from the plant species *Sambucus nigra, Centella asiatica* and *Echinacea purpurea*, and excipients, said excipients comprising a bulk ingredient, an adhesive polymer of acrylic acid and polyvinylpyrrolidone.

11. A method according to claim 10, wherein said mucosal tissue is selected from the group consisting of buccal mucosal tissue, vaginal mucosal tissue, and anal mucosal tissue.

12. A method according to claim 10, wherein said muco-adhesive composition is provided in the form of a tablet, and wherein a surface of the tablet is partially coated with a non-adhesive material, such that said tablet is provided with a first, adhesive side and a second, coated, non-adhesive side.

13. A method according to claim 12 comprising contacting the first, adhesive side of the tablet with the mucosal tissue lesion, wherein the coated non-adhesive side projects away from said lesion.

14. A method according to claim 12, wherein an amount of said *Sambucus nigra* extract ranges between about 0.05 mg to about 15 mg, wherein an amount of said *Centella asiatica* extract ranges between about 0.05 mg to about 15 mg, and wherein an amount of said *Echinacea purpurea* extract ranges between about 0.05 mg to about 15 mg.

15. A method according to claim 10, wherein the step of contacting occurs for a period of time ranging between about 1 hour and about 5 hours.

* * * * *